United States Patent [19]
Abrams

[11] Patent Number: 5,135,503
[45] Date of Patent: Aug. 4, 1992

[54] SHAPING RIBBON FOR GUIDING MEMBERS

[75] Inventor: Robert M. Abrams, Mountain View, Calif.

[73] Assignee: Advanced Cardiovascular Systems, Inc., Santa Clara, Calif.

[21] Appl. No.: 524,345

[22] Filed: May 16, 1990

[51] Int. Cl.⁵ .............................................. A61B 6/00
[52] U.S. Cl. ................................... 604/164; 128/772
[58] Field of Search ..................... 604/164, 95, 96; 128/772

[56] References Cited

U.S. PATENT DOCUMENTS

| | | | |
|---|---|---|---|
| 4,554,929 | 11/1985 | Samson et al. | 604/164 |
| 4,721,117 | 1/1988 | Mar | 604/164 |
| 4,771,778 | 9/1988 | Mar | 604/164 |
| 4,922,924 | 5/1990 | Gambale et al. | 604/164 |
| 4,940,062 | 7/1990 | Hampton et al. | 604/95 |
| 4,953,553 | 9/1990 | Tremulis | 128/772 |
| 4,955,384 | 9/1990 | Taylor | 604/164 |
| 4,998,916 | 3/1991 | Hammerslag et al. | 604/164 |
| 4,998,923 | 3/1991 | Samson et al. | 604/95 |

*Primary Examiner*—Paul J. Hirsch
*Attorney, Agent, or Firm*—Crosby, Heafey, Roach & May

[57] ABSTRACT

A shaping ribbon for intravascular guiding members such as guidewires which is formed from an alloy containing about 3 to about 30% rhenium and the balance essentially of tungsten and has a tensile strength of about 200 to about 600 ksi. The ribbon has a rectangular transverse cross section and the distal end of the ribbon is readily secured by laser or plasma arc welding to the distal end of a helical coil. Its proximal end is secured to the core element at an intermediate location by soldering or brazing. The ribbon has excellent strength and torque resistance.

13 Claims, 1 Drawing Sheet

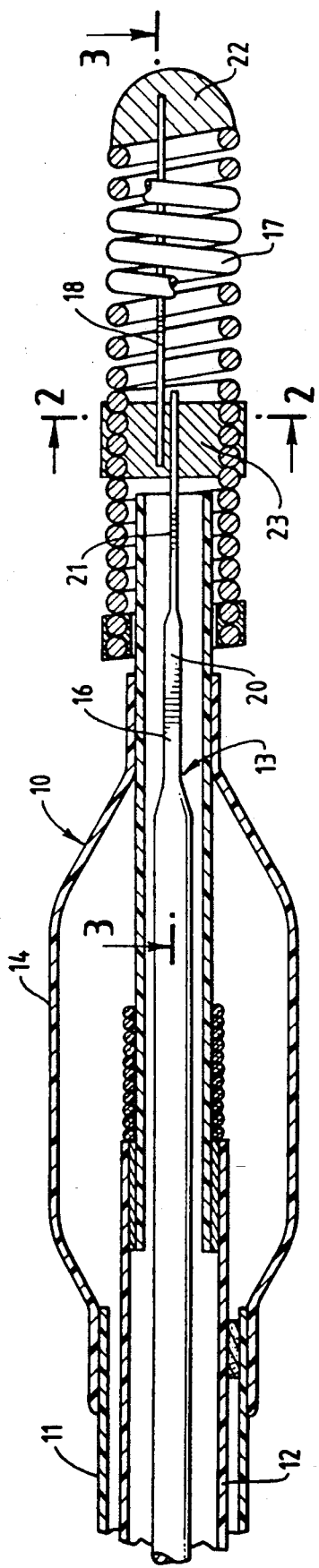
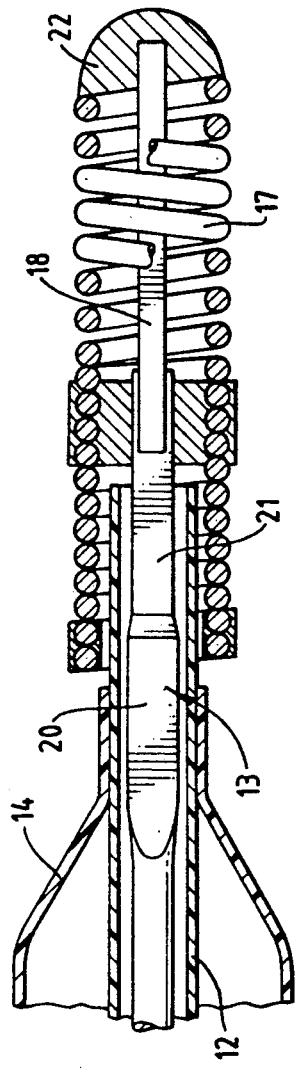
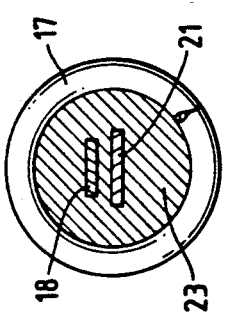

SHAPING RIBBON FOR GUIDING MEMBERS

BACKGROUND OF THE INVENTION

This invention is generally directed to guidewires and guiding members for dilatation catheters which are suitable for percutaneous transluminal coronary angioplasty (PTCA).

In typical PTCA procedures a dilatation catheter having an inflatable, relatively inelastic balloon on the distal end thereof is advanced through a patient's arterial system until the balloon crosses the atherosclerotic lesion to be dilated. The balloon is inflated to a predetermined size with radiopaque liquid by a syringe-like inflation device mounted on the proximal end of the catheter to dilate the lesion and then it is deflated so that the catheter can be removed and blood flow resumed.

The first step of the procedure is to percutaneously introduce a guiding catheter having a preformed distal tip into the patient's arterial system (e.g.the femoral artery) and advance it therein until the preformed distal tip is seated within the ostium of the patient's appropriate coronary artery. In over-the-wire systems a guidewire is usually preloaded within an inner lumen of the dilatation catheter and both are advanced through the previously positioned guiding catheter to the distal end thereof. The guidewire is first advanced out of the distal tip of the guiding catheter into the patient's coronary artery until the distal end of the guidewire crosses the stenotic region to be dilated. The physician usually shapes the distal end of the guidewire to facilitate guiding it through the patient's tortuous coronary anatomy to the stenotic region. When the guidewire is in the desired position, the dilatation catheter is then advanced out of the guiding catheter over the guidewire until the inflatable balloon on the distal end thereof is positioned across the stenosis. The balloon is inflated one or more times to a relatively high pressure (e.g. up to 8 atmospheres or more) by the inflation device to dilate the stenosis. After the stenosis has been dilated, the balloon is deflated and the catheter is removed.

For a more detailed description of angioplasty procedures and the devices used in such procedures, reference is made to U.S. Pat. No. 4,323,071 (Simpson-Robert); U.S. Pat. No. 4,332,254 (Lundquist); U.S. Pat. No. 4,439,185 (Lundquist); U.S. Pat. No. 4,468,224 (Enzmann et al.); U.S. Pat. No. 4,516,972 (Samson); U.S. Pat. No. 4,538,622 (Samson et al.); and U.S. Pat. No. 4,616,652 (Simpson) which are hereby incorporated herein in their entirety.

Steerable dilatation catheters with built-in or fixed guidewires or guiding elements are frequently used because the deflated profile of such catheters are generally much smaller than conventional dilatation catheters having the same inflated balloon size. Further details of low-profile steerable dilatation catheters may be found in U.S. Pat. No. 4,582,181 (Samson), U.S. Pat. No. 4,771,778 (Mar), and U.S. Pat. No. 4,793,350 (Mar et al.) and copending application Ser. No. 287,772, filed Dec. 21, 1988, which are hereby incorporated in their entirety by reference thereto. The low profile and improved pushability of these catheters allows them to cross tighter lesions and to be advanced much deeper into the patient's coronary anatomy. Moreover, the use of steerable, low-profile dilatation catheters having a built-in guidewire or guiding element shortens the time for angioplasty procedures because there is no need to first advance a guidewire out the distal end of the guiding catheter into the patient's coronary artery and then advance a dilatation catheter over the previously positioned guidewire.

Guiding members and guidewires used in angioplasty procedures generally include an elongated core member with a flexible helical coil secured to the distal extremity of the core member. The core member can extend to the distal end of the coil and be secured thereto or the distal extension of the core element can terminate short of the distal end of the coil and a thin, flat shaping ribbon can extend to the distal end of the coil and be secured by its distal end thereto. In the latter instance the ribbon is secured, usually by soldering or brazing, by its proximal end to the core element. Welding could be employed, but the physical properties in the heat affected zone of the weldment would be reduced to unacceptable levels for the intended uses of the product. Even when low temperature bonding methods such as soldering or brazing are used, the prior art ribbons frequently had limited resistance to torquing.

What has been needed and heretofore unavailable is an improved distal structure for guiding members such as guidewires which has the strength to withstand extensive torquing with little or no loss in flexibility and which can be easily shaped by the physician before inserting the guiding member into the patient. The present invention satisfies this need.

SUMMARY OF THE INVENTION

This invention is directed to the distal construction of guiding members or guidewires, and particularly to shaping elements such as ribbons employed in such constructions.

The guiding member of the present invention generally includes an elongated core element with a tapered distal extremity, a flexible body such as helical coil disposed about the distal extremity of the core element and a shaping ribbon extending from the tapered distal extremity of the core to the distal end of the flexible body.

The shaping ribbon is formed of an alloy of tungsten and rhenium and particularly an alloy containing from about 3 to about 30% of rhenium and the balance essentially tungsten. All percentages given herein with respect to composition are weight percent unless otherwise noted. The alloy is preferably a high purity, essentially binary alloy with less than about 50 ppm each and 500 ppm total of other elements. Impurities such as potassium, sodium, iron, nickel, silicon, aluminum and copper should not exceed 25 parts per million. The ribbon will typically have a length of about 1.5 to about 4 cm and a rectangular shaped transverse cross section with a thickness of about 0.0005 to about 0.0025 inch (0.013–0.064 mm) and a width of about 0.002 to about 0.004 inch (0.051–0.102 mm). Other sizes and shapes can be employed depending upon the end uses thereof.

The shaping ribbon of the present invention has very a high tensile strength in the longitudinal direction, e.g. about 200 to about 600 ksi in a cold worked condition (1.38–4.14 MPa), and an elongation of at least 0.8% and preferably about 1 to about 5%. The distal end of the ribbon can be readily welded by suitable means such as laser or plasma arc welding with little or no loss in strength or other mechanical properties to the distal end of the coil. The distal guide wire construction with such a ribbon has improved reliability because of increased torque resistance and it can be readily shaped by the physician. These and other advantages of the invention will become more apparent from the following detailed description thereof when taken in conjunction with the accompanying exemplary drawings.

BRIEF DESCRIPTION OF THE DRAWINGS

FIG. 1 is an elevational view in section of a steerable dilatation catheter embodying features of the invention;

FIG. 2 is a transverse cross sectional view taken along the line 2—2 shown is FIG. 1; and FIG. 3 is a longitudinal view taken along the line 3—3 shown in FIG. 1.

DETAILED DESCRIPTION OF THE INVENTION

Reference is made to FIG. 1 which illustrates the distal end of a steerable dilatation catheter 10 embodying features of the invention. As shown, the catheter 10 comprises a outer tubular member 11, an inner tubular member 12, disposed within the outer tubular member, a guiding member 13 and an inflatable, relatively inelastic balloon 14 which is secured by its proximal end to the distal end of the outer tubular member 11 and by its distal end to the distal end of the inner tubular member 12.

The guiding member 13 includes a core element 15 with a tapered distal section 16, a coil element 17 and a shaping ribbon 18. The tapered section 16 of the core member 15 includes flattened sections 20 and 21. The distal end of shaping ribbon 18 is joined to the distal end of the coil 17 by plasma welding which forms rounded plug 22. The proximal end of the shaping ribbon 18 is secured to tapered section 16 of the core element 15 and the coil element 17 at an intermediate location 23 by suitable means such as brazing or soldering. The last few turns of the proximal end of the coil element 17 are joined together by suitable means such as adhesive. Preferably, the proximal end of the coil is not fixed to the inner tubular member 12 or the distal end of the balloon to allow the free rotation of the coil.

The shaping ribbon 18 of the invention is preferably cold worked by drawing an extruded W-Re alloy rod about 0.02 inch (0.51 mm) in diameter in a series of drawing operations to a final wire diameter of about 0.001 to about 0.005 inch (0.025–0.127 mm) typically about 0.003 inch (0.076 mm). The final drawing is conducted cold or at about 200 degrees F., and the product is annealed after reductions in cross-section of about 30 to about 50%. The extruded rod from which the wire is drawn is preferably prepared from an ingot formed by powder metallurgical techniques. The rod is commercially available from the Sandvick Rhenium Corporation with rhenium contents of 3%, 5%, and 25% rhenium and the balance tungsten. The latter composition is preferred. Rhenium contents above 27% increase the risk of sigma phase embrittlement. After the wire is drawn, it is rolled to its final shape with a rectangular cross section of about 0.001 by about 0.003 inch (0.025 by 0.076 mm). It is in this shape that the ribbon 18 is secured to the core element and the coil 17.

The coil 17 can be made of a wide variety of suitable materials such as stainless steel, platinum, palladium and the like. A particularly suitable alloy consists essentially of about 45 to about 65% palladium, about 25 to about 45% platinum and about 3 to about 15% molybdenum. A presently preferred alloy contains 56% palladium, 38% platinum and 6% molybdenum. The core element 15 can be made of suitable material such as stainless steel, Nitinol (a super elastic alloy containing nickel and titanium) or high strength composites.

The catheter and guidewire constructions employing the ribbon of the invention can be of conventional design. A presently preferred steerable catheter employing the ribbon of the invention is disclosed in copending application Ser. No. 287,772 filed Dec. 21, 1988, now U.S. Pat. No. 4,998,917, which has been incorporated herein. The size and characteristics of the guiding member and/or catheter will depend upon the end use (e.g. coronary or peripheral vascular use) as will be appreciated by those skilled in the art.

The ribbon of the present invention is characterized by greatly increased strength and torsion resistance over conventional materials as shown in the following table. Moreover, it can be easily shaped by hand. The values reported are typical values.

| COMPOSITION | TENSILE STRENGTH | TURNS TO FAILURE |
|---|---|---|
| Tungsten | 0.75 lbs. | 12 |
| 304 SS | 1.01 lbs. | 30 |
| 75% W- 25% Re | 1.43 lbs. | 75 |

While the description of the present invention has been primarily directed to a distal guidewire construction for steerable, fixed-wire dilatation catheters, those skilled in the art will recognize that various modifications can be made to the invention. For example, the ribbon of the invention can be incorporated into guidewires in over-the-wire dilatation catheter systems. Other modifications and improvements can be made to the invention without departing from the scope thereof.

What is claimed is:

1. An intravascular guiding member comprising:
   a) an elongated core element having proximal and distal ends;
   b) a flexible body disposed about the distal end of the core element having a distal end spaced from the distal end of the core element; and
   c) a shaping ribbon formed of an alloy consisting essentially of tungsten and from about 3 to about 30% rhenium which has a tensile strength in the longitudinal direction of about 200 to about 600 ksi and an elongation of about 0.8 to about 5% and which is secured by the distal end thereof to the distal end of the flexible body and by the proximal end thereof to the core element.

2. The guiding member of claim 1 wherein the shaping ribbon is cold worked.

3. The guiding member of claim 1 wherein the ribbon is about 1.5 to about 4 cm in length and has a transverse rectangular cross section.

4. The guiding member of claim 3 wherein the ribbon is about 0.0005 to about 0.0025 inch thick and about 0.002 to about 0.004 inch wide.

5. The guiding member of claim 1 wherein the flexible body disposed about the distal end of the core element is helical coil.

6. The guiding member of claim 5 wherein the helical coil is formed from a wire comprising an alloy of palladium, platinum and molybdenum.

7. The guiding member of claim 6 wherein the helical coil alloy consists essentially of about 45 to about 65% palladium, about 25 to about 45% platinum and about 3 to about 15% molybdenum.

8. The guiding member of claim 6 wherein the shaping ribbon alloy contains less than 50 parts per million each of potassium, sodium, iron, nickel, silicon, aluminum and copper.

9. The guiding member of claim 1 wherein the distal end of the ribbon is welded to the distal end of the flexible body to form a rounded plug.

10. The guiding member of claim 1 wherein the core member has a flattened distal end.

11. A steerable dilation catheter comprising:
 a) an elongated outer tubular member which has an inner lumen extending therein;
 b) an inflatable balloon on the distal end of the outer tubular member having an interior in fluid communication with the inner lumen of the outer tubular member;
 c) a steerable guiding member as in claim 1 extending through the interior of the balloon with the portion of the guiding member having the flexible body extending out the distal end of the balloon thereof and with means to seal the distal end of the balloon.

12. The dilation catheter of claim 11 including an inner tubular member disposed within the outer tubular member.

13. The dilation catheter of claim 12 wherein the distal end of the balloon is sealingly bonded to the distal end of the inner tubular member.

* * * * *